(12) United States Patent
Meyer et al.

(10) Patent No.: US 11,547,644 B2
(45) Date of Patent: Jan. 10, 2023

(54) EMULSIONS COMPRISING CATIONIC EMULSIFIERS BASED ON MDIPA ESTER QUATS

(71) Applicant: Evonik Operations GmbH, Essen (DE)

(72) Inventors: Juergen Meyer, Essen (DE); Anna M. Howe, Moseley, VA (US); Maria L. Spohrer, Glen Allen, VA (US); Hans-Juergen Koehle, Mainhausen (DE); Brajesh Kumar Jha, Midlothian, VA (US)

(73) Assignee: Evonik Operations GmbH, Essen (DE)

( * ) Notice: Subject to any disclaimer, the term of this patent is extended or adjusted under 35 U.S.C. 154(b) by 225 days.

(21) Appl. No.: 15/201,898

(22) Filed: Jul. 5, 2016

(65) Prior Publication Data
US 2017/0000709 A1 Jan. 5, 2017

(30) Foreign Application Priority Data
Jul. 2, 2015 (EP) .................................... 15174954

(51) Int. Cl.
| | |
|---|---|
| A61K 8/06 | (2006.01) |
| A61K 8/41 | (2006.01) |
| A61K 8/37 | (2006.01) |
| A61Q 19/00 | (2006.01) |
| A61K 8/34 | (2006.01) |
| A61K 8/891 | (2006.01) |
| A61K 8/92 | (2006.01) |
| A61Q 1/02 | (2006.01) |
| A61Q 15/00 | (2006.01) |
| A61Q 17/04 | (2006.01) |

(52) U.S. Cl.
CPC .............. A61K 8/416 (2013.01); A61K 8/06 (2013.01); A61K 8/062 (2013.01); A61K 8/342 (2013.01); A61K 8/375 (2013.01); A61K 8/891 (2013.01); A61K 8/92 (2013.01); A61Q 1/02 (2013.01); A61Q 15/00 (2013.01); A61Q 17/04 (2013.01); A61Q 19/00 (2013.01); A61K 2800/30 (2013.01); A61K 2800/48 (2013.01)

(58) Field of Classification Search
None
See application file for complete search history.

(56) References Cited

U.S. PATENT DOCUMENTS

| 5,296,622 | A | * | 3/1994 | Uphues | ................. | C07C 219/08 |
| | | | | | | 554/103 |
| 6,562,780 | B2 | * | 5/2003 | Bermejo | ................. | C11D 1/835 |
| | | | | | | 510/499 |
| 9,763,870 | B2 | * | 9/2017 | Schwab | ................... | A61Q 5/12 |
| 9,801,797 | B2 | * | 10/2017 | Koehle | ................... | A61K 8/342 |
| 2005/0288198 | A1 | * | 12/2005 | Pereira | ..................... | A61K 8/45 |
| | | | | | | 510/130 |
| 2007/0231289 | A1 | | 10/2007 | Gruning et al. | | |
| 2008/0317687 | A1 | * | 12/2008 | Howe | ...................... | A61K 8/06 |
| | | | | | | 424/59 |
| 2014/0286889 | A1 | * | 9/2014 | Koehle | .................. | A61K 8/342 |
| | | | | | | 424/70.28 |

FOREIGN PATENT DOCUMENTS

| EP | 1 844 753 A2 | 10/2007 |
| EP | 1 844 753 A3 | 10/2007 |
| EP | 2 783 677 A2 | 10/2014 |
| EP | 2 783 677 A3 | 10/2014 |
| WO | WO 2004/093834 A1 | 11/2004 |

OTHER PUBLICATIONS

Kamal-Eldin, Afaf; "Effect of fatty acids and tocopherols on the oxidative stability of vegetable oils," 2006, WILEY-VCH; European Journal of Lipid Science and Technology, vol. 108, Issue 12, pp. 1051-1061. (Year: 2006).*
Moser, Bryan R.; "Comparative Oxidation Stability of Fatty Acid Alkyl Esters by Accelerated Methods," 2009; Springer; Journal of the American Oil Chemists' Society vol. 86, Issue 7, pp. 699-706. (Year: 2009).*
European Search Report dated Dec. 14, 2015 in Patent Application No. 15174954.6 (with English Translation of Categories of Cited Documents).

* cited by examiner

Primary Examiner — Tigabu Kassa
Assistant Examiner — Ivan A Greene
(74) Attorney, Agent, or Firm — Oblon, McClelland, Maier & Neustadt, L.L.P.

(57) ABSTRACT

An emulsion contains A) an alkyl ester quat of formula I

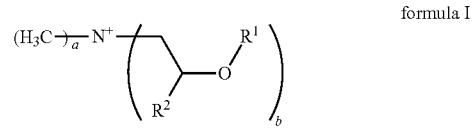

formula I wherein $R^1$ is an acyl radical of a fatty acid with a chain length of from 6 to 24 carbon atoms, with the proviso that a mass fraction of saturated, linear fatty acids with a chain length of from 12 to 24 carbon atoms, is more than 50% by weight, based on all acyl radicals $R^1$, wherein $R^2$ is an alkyl radical having 1 to 6 carbon atoms, wherein a=1-3 and b=1-3, with the proviso that a+b=4, B) at least one consistency regulator, and C) at least one cosmetic oil.

9 Claims, No Drawings

EMULSIONS COMPRISING CATIONIC EMULSIFIERS BASED ON MDIPA ESTER QUATS

BACKGROUND OF THE INVENTION

Field of the Invention

The invention relates to an emulsion comprising a certain alkyl ester quat, consistency regulator and cosmetic oil.

Discussion of the Background

The invention enables the preparation of cosmetic emulsions that have long-term stability and have a pleasantly dry skin feel with simultaneously considerably improved biodegradability and ecotoxicity of the cationic emulsifier used compared to the related art.

Cationic emulsions have been used for many years primarily in North America, but increasingly also in other regions, especially in the area of cosmetic skincare. The particular advantage of these systems is that, even when using extremely rich oils such as petrolatum or mineral oil, they exhibit rapid absorption into the skin and leave behind a very dry skin feel. Furthermore, these emulsions are characterized in that they have a long-lasting moisturizing effect. Moreover, they exhibit film-forming properties which make them of interest in principle also for sun protection applications.

U.S. Pat. No. 4,389,418 describes skincare compositions based on petrolatum or mineral oil, a cationic emulsifier, fatty alcohol and an ester oil. These compositions have moisturizing properties but at the same time also exhibit a non-greasy, pleasant sensory effect upon application to the skin.

The emulsions described in U.S. Pat. No. 4,389,418 are based on dimethyldialkylammonium salts, preferably on dimethyldistearylammonium chlorides (distearyldimonium chloride).

On account of the very good emulsifying performance of this emulsifier and the corresponding storage stability and flexibility of these emulsions, distearyldimonium chloride has hitherto been the most used emulsifier for cationic emulsions for cosmetic applications.

However, in recent years questions relating to the sustainability and environmental compatibility of cosmetic products have become increasingly important. Cosmetic ingredients should preferably be characterized by good biodegradability and low environmental toxicity. These properties of possible cationic emulsifiers should of course be improved but the application properties of the cosmetic emulsions produced therewith should in no way be restricted.

Possible alternatives described hitherto for such cationic emulsion systems for cosmetic applications are primarily ester quats which are obtainable by esterification of fatty acids with a chain length of C16-C22 with triethanolamine or methyldiethanolamine and subsequent quaternization.

U.S. Pat. No. 7,597,881 describes sunscreen emulsions primarily based on such ester quats which have a sand-repellent effect.

However, emulsions based on such ester quats exhibit stability problems upon long-term storage, especially at elevated temperatures. For this reason, the use of ester quats in cosmetic emulsions for applications to the skin has hitherto not become established in the market.

EP2783677 describes cosmetic formulations comprising ester quats based on isopropanolamine, and the use of these ester quats in cosmetics. The described ester quats here comprise alkyl radicals with at least one unsaturated fatty acid having a chain length of from 18 to 24 carbon atoms or an acyl radical of isostearic acid or ricinoleic acid. Such ester quats are suitable for cosmetic haircare products. However, they do not exhibit adequate stabilization of cosmetic emulsions and are therefore unsuitable for producing cationic emulsions for skincare applications.

SUMMARY OF THE INVENTION

It was therefore an object of the invention to develop emulsions that have long-term stability and are based on cationic emulsifiers which permit considerably better emulsion stabilization than the systems based on ester quats described hitherto.

Surprisingly, it has been found that the emulsions described hereinbelow are able to solve the problem addressed by the invention.

The present invention therefore provides an emulsion, comprising:
A) an alkyl ester quat of formula I

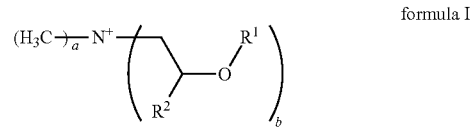

formula I wherein $R^1$ is an acyl radical of a fatty acid with a chain length of from 6 to 24 carbon atoms, with the proviso that a mass fraction of saturated, linear fatty acids with a chain length of from 12 to 24 carbon atoms, is more than 50% by weight, based on all acyl radicals $R^1$, wherein $R^2$ is an alkyl radical having 1 to 6 carbon atoms, wherein a=1-3 and b=1-3, with the proviso that a+b=4, B) at least one consistency regulator, and
C) at least one cosmetic oil.

The present invention also provides a cosmetic care and/or cleaning formulation, comprising:
the above emulsion.

Further, the present invention provides an emulsifier, comprising:
an alkyl ester quat of formula I

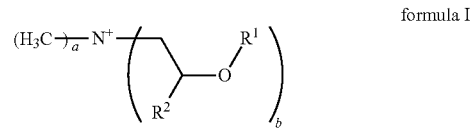

formula I wherein $R^1$ is an acyl radical of a fatty acid with a chain length of from 6 to 24 carbon atoms, with the proviso that the mass fraction of saturated, linear fatty acids with a chain length of from 12 to 24 carbon atoms, is more than 50% by weight, based on all of the acyl radicals $R^1$, wherein $R^2$ is an alkyl radical having 1 to 6 carbon atoms.

One advantage of the present invention is that the alkyl ester quats present in the emulsions according to the invention have a considerably better environmental profile than distearyldimonium chloride, the hitherto gold standard of cationic emulsifiers in the cosmetics sector.

It is an advantage of the invention that the emulsions according to the invention exhibit an advantageous, pleasantly light, non-sticky skin feel. This skin feel advantageously corresponds here to the skin feel which systems with distearyldimonium chloride also typically have. Consequently, classic emulsion systems based on distearyldimonium chloride can be converted in a simple manner into more environmentally friendly emulsion systems with comparable application properties.

A further advantage of the present invention is that the alkyl ester quats used in the emulsions according to the invention can usually be prepared completely free from solvents, whereas the distearyldimonium chloride typically used in cosmetics comprises small residual amounts of solvents such as e.g. isopropyl alcohol.

Also advantageous is in particular the large formulation flexibility of the emulsions according to the invention, meaning that tailored formulations can easily be developed for a broad field of applications based on these emulsions. In this connection, advantages as regards the water resistance of these formulations compared to other formulation concepts can be observed in the field of sun protection and make-up in particular.

DETAILED DESCRIPTION OF THE INVENTION

The present invention therefore provides an emulsion comprising
A) alkyl ester quats of the general formula I

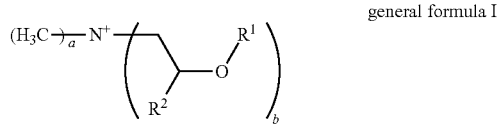

general formula I where $R^1$ is an acyl radical of a fatty acid having a chain length of from 6 to 24 carbon atoms, preferably 12 to 22 carbon atoms, in particular 16 to 18 carbon atoms, with the proviso that the mass fraction of saturated, linear fatty acids with a chain length of from 12 to 24 carbon atoms, preferably 14 to 22 carbon atoms, in particular 16 to 18 carbon atoms, is more than 50% by weight, preferably more than 55% by weight, very particularly preferably more than 60% by weight, based on all of the acyl radicals $R^1$, where $R^2$ is an alkyl radical having 1 to 6 carbon atoms, preferably methyl, ethyl, propyl or isopropyl, particularly preferably methyl, where $a=1-3$ and $b=1-3$, preferably $a=1.8-2.2$ and $b=1.8-2.2$, particularly preferably $a=b=2$, with the proviso that $a+b=4$, B) at least one consistency regulator, and
C) at least one cosmetic oil.

The present invention also relates to the above emulsion characterized in that
A) in an amount of from 0.2% by weight to 10% by weight, preferably from 0.5% by weight to 7% by weight, in particular from 1% by weight to 6% by weight, B) in an amount of from 0.5% by weight to 10% by weight, preferably from 2% by weight to 8% by weight, in particular from 3% by weight to 6% by weight, and
C) in an amount of from 5% by weight to 40% by weight, preferably from 6% by weight to 35% by weight, in particular from 8% by weight to 30% by weight, is present, where the percent by weight refer to the total emulsion.

In another embodiment, the above emulsion is characterized in that
A) alkyl ester quats of the general formula I
where $R^1$ is an acyl radical of a fatty acid having a chain length of from 6 to 24, with the proviso that the mass fraction of saturated, linear fatty acids with a chain length of from 16 to 18 carbon atoms is more than 60% by weight, based on all of the acyl radicals $R^1$,
where $R^2$ is methyl,
where $a=1.8-2.2$ and $b=1.8-2.2$, with the proviso that $a+b=4$.

In yet another embodiment, the above emulsion is characterized in that
A) alkyl ester quats of the general formula I
where $R^1$ is an acyl radical of a fatty acid having a chain length of from 6 to 24, with the proviso that the mass fraction of saturated, linear fatty acids with a chain length of 18 carbon atoms is more than 60% by weight, based on all of the acyl radicals $R^1$,
where $R^2$ is methyl,
where $a=1.8-2.2$ and $b=1.8-2.2$, with the proviso that $a+b=4$.

In another embodiment, the above emulsion is characterized in that the mass fraction of radicals $R^1$ from unsaturated, linear fatty acids having a chain length of from 12 to 24 carbon atoms, preferably 14 to 22 carbon atoms, in particular 16 to 18 carbon atoms, is from 5% by weight to 35% by weight, preferably from 10% by weight to 30% by weight, very particularly preferably from 15% by weight to 25% by weight, based on all of the acyl radicals $R^1$.

In another embodiment, the above emulsion is characterized in that the consistency regulator is selected from the group consisting of fatty alcohols having 12 to 24 carbon atoms, preferably 14 to 22 carbon atoms, particularly preferably 16-18 carbon atoms,
glycerol esters and polyglyceryl esters,
fatty acids having 12 to 24 carbon atoms and
polymer-based thickeners.

In another embodiment, the above emulsion is characterized in that the cosmetic oil is selected from the group consisting of silicone oils, functionalized silicones, mineral oils, fatty acid esters, fatty alcohol ethers, natural oils such as vegetable oils, animal oils and mixtures thereof.

Further, the above emulsion is characterized in that it is a cosmetic care and cleaning formulation, in particular for skin and skin appendages.

In addition, the present invention relates to the use of alkyl ester quats of the general formula I as emulsifier.

Mixtures of ester quats which may be present in the emulsions according to the invention are of course encompassed; data relating to the number of units (specifically the values a and b) which may be present multiple times in the ester quats are to be understood as average values, averaged over all of the corresponding compounds.

The emulsions comprise e.g. the components A), B) and C). Preferred embodiments of the emulsions according to the invention in which only part ranges of the components A), B) or C) are present are naturally automatically free from components of the less preferred ranges.

Thus, e.g. preferred emulsions in which A) alkyl ester quats of the general formula I where $R^1$ is an acyl radical of the fatty acid with a chain length of from 12 to 22 carbon atoms are present comprise no alkyl ester quats of the general formula I where $R^1$ is an acyl radical of a fatty acid with a chain length of from 6 to 11 and 23 to 24 carbon atoms.

Unless otherwise stated, all percentages (%) given are percentages by weight.

It is preferred according to the invention if the mass fraction of radicals $R^1$ from unsaturated, linear fatty acids with a chain length of from 12 to 24 carbon atoms, preferably 14 to 22 carbon atoms, in particular 16 to 18 carbon atoms, is from 5% by weight to 35% by weight, preferably from 10% by weight to 30% by weight, very particularly preferably from 15% by weight to 25% by weight, based on all of the acyl radicals $R^1$.

Preferred emulsions according to the invention are characterized in that
- A) in an amount of from 0.2% by weight to 10% by weight, preferably from 0.5% by weight to 7% by weight, in particular from 1% by weight to 6% by weight,
- B) in an amount of from 0.5% by weight to 10% by weight, preferably from 2% by weight to 8% by weight, in particular from 3% by weight to 6% by weight, and
- C) in an amount of from 5% by weight to 40% by weight, preferably from 6% by weight to 35% by weight, in particular from 8% by weight to 30% by weight, is present,
where the percentages by weight refer to the total emulsion.

Particularly preferred emulsions according to the invention comprise
- A) alkyl ester quats of the general formula I
where $R^1$ is an acyl radical of a fatty acid with a chain length of from 6 to 24, with the proviso that the mass fraction of saturated, linear fatty acids with a chain length of from 16 to 18 carbon atoms is more than 60% by weight, based on all of the acyl radicals $R^1$,
where $R^2$ is methyl,
where $a=1.8-2.2$ and $b=1.8-2.2$, with the proviso that $a+b=4$.

In this connection, it is particularly preferred if the mass fraction of radicals $R^1$ from unsaturated, linear fatty acids of 16 to 18 carbon atoms is from 15% by weight to 30% by weight, based on all of the acyl radicals $R^1$.

Very particularly preferred emulsions according to the invention comprise
- A) alkyl ester quats of the general formula I
where $R^1$ is an acyl radical of a fatty acid with a chain length of from 6 to 24, with the proviso that the mass fraction of saturated, linear fatty acids with a chain length of 18 carbon atoms is more than 60% by weight, based on all of the acyl radicals $R^1$,
where $R^2$ is methyl,
where $a=1.8-2.2$ and $b=1.8-2.2$, with the proviso that $a+b=4$.

In this connection, it is particularly preferred if the mass fraction of radicals $R^1$ from unsaturated, linear fatty acids of 18 carbon atoms is from 15% by weight to 30% by weight, based on all of the acyl radicals $R^1$.

Preferred consistency regulators that are preferably present in the emulsions according to the invention are selected from the group consisting of fatty alcohols having 12 to 24 carbon atoms, preferably 14 to 22 carbon atoms, particularly preferably 16-18 carbon atoms,
glyceryl esters and polyglyceryl esters,
fatty acids having 12 to 24 carbon atoms and
polymer-based thickeners.

The consistency regulators here are, for example:
Fatty alcohols having 12 to 24 carbon atoms, preferably 14 to 22, particularly preferably 16-18,
Glyceryl esters or polyglyceryl esters, preferably having an average degree of polymerization of at most 4, with at least one alkyl chain having 12 to 24 carbon atoms, preferably 14 to 22, particularly preferably 16-18,
Fatty acids having 12 to 24 carbon atoms, preferably 14 to 22, particularly preferably 16-18,
Polymer-based thickeners such as e.g. cellulose, cellulose derivatives such as e.g. hydroxyethylcellulose, hydroxypropylcellulose, alkyl-modified cellulose types, such as, for example, cetylhydroxyethylcellulose, guar, alkyl-modified guar types, such as, for example, C18-22 hydroxylalkyl hydroxypropyl guar, starch derivatives, alkyl-modified starch derivatives, xanthan gum, gellan gum, and also polyquaternium compounds such as, for example, polyquaternium-37.

Cosmetic oils that can be used are substances such as silicone oils, functionalized silicones, mineral oils, fatty acid esters, fatty alcohol ethers, natural oils such as vegetable oils, animal oils, and mixtures thereof.

Preferred oils which are preferably present in the emulsions according to the invention are selected from the group consisting of
silicone oils, functionalized silicones, mineral oils, fatty acid esters, fatty alcohol ethers, natural oils such as vegetable oils, animal oils.

Preferred emulsions according to the invention comprise, as cosmetic oil, at least one selected from the group comprising, preferably consisting of, cyclopentasiloxane, cyclomethicone, dimethicone, dimethiconol, amodimethicone, PEG/PPG dimethicones, cetyl dimethicone, stearyl dimethicone, stearoxy dimethicone, behenoxy dimethicone, polyisobutene, petrolatum, mineral oil, hydrogenated polydodecene, hydrogenated polydecene, polydecene, isoamyl cocoate, PPG-3 myristyl ether, PPG-11 stearyl ether, dicaprylyl ether, dicaprylyl carbonate, cetearyl isononanoate, cetyl ethylhexanoate, diethyhexyl carbonate, cetyl ricinoleate, myristyl myristate, stearyl heptanoate, decyl cocoate, decyl oleate, ppg-15 stearyl ether, octyldodecanol, isocetyl palmitate, cetearyl ethylhexanoate, ethylhexyl palmitate, ethylhexyl stearate, isopropyl palmitate, PPG-14 butyl ether, triisostearin, C12-15 alkyl benzoate, phenoxyethyl caprylate, isopropyl myristate, isoamyl cocoate, caprylic/capric triglyceride, sunflower oil, olive oil, argan oil, mineral oil, castor oil, ricinus oil, cocoa oil, palm oil, coconut oil, avocado oil, almond oil, jojoba oil, corn oil, rapeseed oil, sesame oil, soybean oil, wheat germ oil, walnut oil and oleyl erucate.

The emulsions according to the invention are preferably oil-in-water (O/W) emulsions.

The emulsions according to the invention therefore preferably comprise water, in particular in an amount of from 20% by weight to 90% by weight, preferably 30% by weight to 85% by weight, particularly preferably 50% by weight to 80% by weight, where the percentages by weight refer to the total emulsion.

The emulsions according to the invention are in particular cosmetic care and cleaning formulations, in particular for skin and skin appendages. The use of the emulsions according to the invention is also advantageous in sun protection, make-up and antiperspirant/deodorant products.

The term "care formulation" is understood here as meaning a formulation which satisfies the purpose of retaining an article in its original form, of reducing or avoiding the effects of external influences (e.g. time, light, temperature, pressure, soiling, chemical reaction with other reactive compounds that come into contact with the article) such as, for example, ageing, soiling, material fatigue, bleaching, or even of improving desired positive properties of the article.

Emulsions according to the invention thus comprise in particular creams, lotions and sprays for body care, face care, hand care and foot care, sun protection emulsions, make-up emulsions, mascara products, antiperspirant/deodorant emulsions, sera, impregnation emulsions for wet wipes, make-up removers, BB (blemish balm) or CC (color control) creams. The use of the emulsions according to the invention is also possible as leave-in conditioner, hair treatment or in oil-containing shampoos and shower baths.

Cosmetic care and cleaning formulations according to the invention can for example comprise at least one additional component selected from the group of:
nonionic surfactants,
emollients,
emulsifiers,
thickeners/viscosity regulators/stabilizers,
antioxidants,
hydrotropes (or polyols),
solids and fillers,
pearlescence additives,
deodorant and antiperspirant active ingredients,
insect repellents,
self-tanning agents,
preservatives,
conditioners,
perfumes,
dyes,
cosmetic active ingredients,
care additives,
superfatting agents,
solvents.

Substances which can be used as exemplary representatives of the individual groups are known to the person skilled in the art and can be found for example in EP2273966A1. This patent application is herewith incorporated as reference and thus forms part of the disclosure.

As regards further optional components and the amounts used of these components, reference is made expressly to the relevant handbooks known to the person skilled in the art, for example K. Schrader, "Grundlagen und Rezepturen der Kosmetika [Fundamentals and formulations of cosmetics]", 2nd edition, pages 329 to 341, Hüthig Buch Verlag Heidelberg.

The amounts of the particular additives are governed by the intended use.

Typical guide formulations for the respective applications are known related art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

The present invention further provides the use of the alkyl ester quats of the general formula I present in the formulations according to the invention as emulsifier, preferably oil-in-water emulsifier, in particular in cosmetic care and cleaning formulations, especially for skin and skin appendages.

The examples listed below illustrate the present invention by way of example, without any intention of restricting the invention, the scope of application of which is apparent from the entirety of the description and the claims, to the embodiments specified in the examples.

EXAMPLES

Example 1

MDIPA Dialkyl Quat with Essentially Stearic Acid 932 g (3.3 mol) of stearic acid (98% pure) are mixed with 253 g (1.72 mol) of methyldiisopropanolamine and heated to 180° C. with stirring. Water of reaction is distilled off continuously. After the majority of the water of reaction has been distilled off at atmospheric pressure, reduced pressure is applied and the acid number of the reaction mixture is reacted away to <7 mg KOH/g. The resulting ester amine is cooled to 60° C. and admixed in portions with 197 g (1.56 mol) of dimethyl sulphate, such that the reaction temperature does not exceed 100° C.

After cooling to room temperature, the total amine number (TAN) and the active content of the finished product were analyzed.

TAN=4.5 mg KOH/g; active content 1.22 meq/g

Example 2

MDIPA Dialkyl Quat with C16-18 Fatty Acid with Unsaturated Fractions (<30% Unsaturated Fraction)

1075 g (3.9 mol) of fatty acid C16-18 and C18 unsaturated (iodine value 20.2) were mixed with 297 g (2.02 mol) of methyldiisopropanolamine and esterified analogously to Example 1.

The acid number of the ester amine was 6.5 mg KOH/g. This mixture was reacted with 229.5 g (1.82 mol) of DMS (dimethyl sulphate) as described in Example 1. The finished product had a TAN of 4.9 mg KOH/g and an active content of 1.29 meq/g.

Example 3

Preparation of "1-propanaminium, 2-hydroxy-N-(2-hydroxypropyl)-N,N-dimethyl, Diester with Palm Fatty Acid, Methyl Sulphate"

1020 g (4 mol) of palmitic acid (technical grade, approx. 98% pure) were admixed with 302 g (2.05 mol) of methyldiisopropanolamine and esterified as described under Example 1. The ester amine had an acid number of 5.6 mg KOH/g. This mixture was alkylated with 240 g (1.90 mol) of dimethyl sulphate as described in Example 1.

The TAN of the finished product was determined with 4.8 mg KOH/g, the active content was 1.33 meq/g.

Example 4

MDIPA Dialkyl Quat Saturated with C22 Fatty Acid 684.6 g (2.0 mol) of behenic acid (Edenor C22 85 GW) were esterified with 152.5 g (1.03 mol) of methyldiisopropanolamine as described in Example 1. The ester amine had an acid number of 6.1 mg KOH/g. The reaction mixture was admixed with 58.4 g (0.464 mol) of DMS and stirred in the temperature range of 80-100° C. for 30 minutes. Then, 100 ml of isopropanol were added and a further 58.4 g (0.464 mol) of DMS was added dropwise such that the temperature can be kept in the range 80-100° C.

The product had a TAN of 5.5 mg KOH/g and an active content of 0.97 meq/g.

Example 5

MDIPA Dialkyl Quat Saturated with Predominantly C12-18 Fatty Acid 887 g (4.0 mol) of coconut fatty acid C12-18 (Edenor K 1218) were mixed with 305 g (2.06 mol) of methyldiisopropanolamine and esterified as described under Example 1. The reaction mixture had an acid number of 5.9 mg KOH/g. The reaction mixture was then alkylated with 233.3 g (1.85 mol) of DMS analogously to Example 1. The finished product had a TAN of 5.2 mg KOH/g and an active content of 1.49 meq/g.

Example 6

MDIPA Dialkyl Quat with Palm Stearic Acid 1378 g (5.17 mol) of palm stearic acid (iodine number 34.2) are admixed with 385.5 g (2.62 mol) of methyldiisopropanolarnine and reacted as described under Example 1. The ester amine had an acid number of 6.7 mg KOH/g. This reaction mixture was alkylated analogously to Example 1 with 300.6 g (2.38 mol) of DMS. The finished product had a TAN of 5.1 mg KOH/g and an active content of 1.32 meq/g.

Comparative Example 1

Preparation of "1-propanaminium, 2-hydroxy-N-(2-hydroxypropyl)-N,N-dimethyl, Diester with Mixed Vegetable Oil Fatty Acid, Methyl Sulphate"

Corresponding to Example 1 of EP2783677, 1120 g (4 mol) of mixed vegetable oil fatty acid were mixed with 302 g (2.05 mol) of methyldiisoproparolamine and heated to 180° C. with stirring. Water of reaction was distilled off continuously. After the majority of the water of reaction had been distilled off at atmospheric pressure, reduced pressure was applied and the acid number of the reaction mixture was reacted away to <7 mg KOH/g. The resulting ester amine was cooled to 60° C. and admixed in portions with 240 g (1.90 mol) of dimethyl sulphate such that the reaction temperature does not exceed 100° C.

After cooling to room temperature, the total amine number (TAN) and the active content of the finished product were analyzed.

TAN=5.0 mg KOH/g; active content 1.27 meq/g (cationic active content according to Epton).

Comparative Example 2

According to INCI Distearoylethyl Dimonium Chloride; Cetearyl Alcohol

Here, the commercial product VARISOFT EQ 65 from Evonik Industries AG was used.

Comparative Example 3

According to INCI Dipalmoylethyl Hydroxyethyl Methylammonium Methosulfate; Isopropanol Here, the commercial product REWOQUAT WE 28 from Evonik Industries AG was used.

Storage Stability

In the formulation examples 1-1 to 1-6, it was shown compared to Examples C1 to C4 that stable O/W emulsions can be prepared with the help of emulsifiers according to the invention. The emulsions were in each case prepared in a classic hot-hot process in which oil and water phase were heated separately to approx. 75° C. Then, the oil phase was added to the water phase with stirring and then homogenized for 60 seconds. Finally, at approx. 30° C., the preservative was added, the mixture was stirred briefly and then the pH was adjusted to approx. 6.

The emulsion examples according to the invention were stable for at least three months at room temperature, 5° C., 40° C. and 45° C. and successfully also withstood a triple freeze-thaw cycle between room temperature and −15° C.

The comparison emulsions not according to the invention, by contrast, rapidly exhibited water separation especially during storage at elevated temperature, and thus no stabilities acceptable for cosmetic formulations.

The selected emulsion formulations correspond here to typical emulsion systems as were for example also used on the basis of the emulsifier distearyldimonium chloride.

TABLE 1a

Comparative experiment relating to emulsion stability

| Formulation example | 1-1 | 1-2 | 1-3 | 1-4 | 1-5 |
|---|---|---|---|---|---|
| Example 1 | 3.75% | | | | |
| Example 2 | | 3.75% | | | |
| Example 3 | | | 3.75% | | |
| Example 4 | | | | 3.75% | |
| Example 5 | | | | | 3.75% |
| Glyceryl Stearate | 1.0% | 1.0% | 1.0% | 1.0% | 1.0% |
| Cetearyl Alcohol | 1.25% | 1.25% | 1.25% | 1.25% | 1.25% |
| Mineral Oil | 4.0% | 4.0% | 4.0% | 4.0% | 4.0% |
| Isopropyl Palmitate | 4.0% | 4.0% | 4.0% | 4.0% | 4.0% |
| Caprylic/Capric Triglyceride | 4.0% | 4.0% | 4.0% | 4.0% | 4.0% |
| Dimethicone | 1.0% | 1.0% | 1.0% | 1.0% | 1.0% |
| Glycerin | 3.0% | 3.0% | 3.0% | 3.0% | 3.0% |
| Demineralized Water | ad 100% | ad 100% | ad 100% | ad 100% | ad 100% |
| Phenoxyethanol Ethylhexylglycerin[1] | 0.7% | 0.7% | 0.7% | 0.7% | 0.7% |
| Sodium Hydroxide (10% aq. pH adjustment to approx. 6) | q.s. | q.s. | q.s. | q.s. | q.s. |
| Stability | Stable | Stable | Stable | Stable | Stable |

[1]Euxyl PE 9010 (Schülke)

TABLE 1b

Comparative experiments relating to emulsion stability

| Formulation example | 1-6 | C1 | C2 | C3 | C4 |
|---|---|---|---|---|---|
| Example 6 | 3.75% | | | | |
| Comparative Example 1 | | 3.75% | | | |
| Comparative Example 2 | | | 3.75% | | 5.75 |
| Comparative Example 3 | | | | 3.75% | |
| Glyceryl Stearate | 1.0% | 1.0% | 1.0% | 1.0% | 0.25 |
| Cetearyl Alcohol | 1.25% | 1.25% | 1.25% | 1.25% | |
| Mineral Oil | 4.0% | 4.0% | 4.0% | 4.0% | 4.0% |
| Isopropyl Palmitate | 4.0% | 4.0% | 4.0% | 4.0% | 4.0% |
| Caprylic/Capric Triglyceride | 4.0% | 4.0% | 4.0% | 4.0% | 4.0% |
| Dimethicone | 1.0% | 1.0% | 1.0% | 1.0% | 1.0% |
| Glycerin | 3.0% | 3.0% | 3.0% | 3.0% | 3.0% |
| Demineralized Water | ad 100% | ad 100% | ad 100% | ad 100% | ad 100% |
| Phenoxyethanol Ethylhexyl-glycerin[1] | 0.7% | 0.7% | 0.7% | 0.7% | 0.7% |
| Sodium Hydroxide (10% ad. pH adjustment to approx. 6) | q.s. | q.s. | q.s. | q.s. | q.s. |
| Stability | Stable | Water separation after 1 week at 45° C. | Water separation after 4 weeks at 45° C. | Water separation after 4 weeks at 45° C. | Water separation after 6 weeks at 45° C. |

[1]Euxyl PE 9010 (Schülke)

Here, the emulsions 1 to 6 according to the invention were also characterized by the typical skin feel as can be attained for example with comparable emulsions based on the emulsifier distearyldimonium chloride. The emulsions have a dry, non-greasy sensory effect and were characterized by rapid absorption into the skin and a dry skin feel after soaking into the skin.

Furthermore, it was to be demonstrated that the emulsifiers according to the invention exhibit a significantly better biodegradability and a significantly better ecotoxicity than the standard of the dialkylquat distearyldimonium chloride hitherto customary in the market.

Consequently, an emulsifier according to the invention (Example 2) was investigated compared to distearyldimonium chloride with the help of various OECD tests. The results reveal a significantly better biodegradability of the emulsifier according to the invention. Furthermore, significantly increased and therefore advantageous limiting values were found for the emulsifier according to the invention from Example 2 for the long-term toxicity towards fish and for the short-term and long-term toxicity towards invertebrate aquatic animals.

TABLE 2

Comparison of the biodegradability and selected ecotoxicity values

| | Distearyldimonium Chloride* | Example 2 |
|---|---|---|
| Biodegradability in water | OECD 301: 3% (28 d) | OECD 301: 60% (28 d) |
| Long-term toxicity towards fish | Fish Early Life Stage Test (OECD 210) (Fathead minnow) NOEC = 0.23 mg/l in standard water | Fish Early Life Stage Test (OECD 210) (Fathead minnow) NOEC = 0.686 mg/l in standard water |
| Short-term toxicity towards invertebrate aquatic animals | Acute Immobilization Test (OECD 202) EC-50(48h) = 0.16 mg/l | Acute Immobilization Test (OECD 202) EC50(48h) = 6.7 mg/l |
| Long-term toxicity towards invertebrate aquatic animals | Daphnia Magna Reproduction Test (OECD 211) NOEC(21 d) = 0.38 mg/l | Daphnia Magna Reproduction Test (OECD 211) NOEC(21 d) = 1 mg/l |

*VARISOFT TA 100 (Evonik Industries AG)

The examples thus demonstrate clearly that the emulsion systems according to the invention offer clear advantages over the known related art in that they show how environmentally friendly cationic emulsion systems can be synthesized for cosmetic care applications.

Further Formulation Examples

The concentration data in the following formulations are in percent by mass.

O/W Lotion

This example is intended to show that it is also very readily possible to add the emulsifier according to the invention to the water phase.

| Example 1 | 5.0% |
|---|---|
| Water | ad 100% |
| Glycerin | 3.0% |
| Glyceryl Stearate[2] | 1.0% |
| Cetearyl Alcohol | 1.25% |
| Stearyl Alcohol | 1.0% |
| Mineral Oil | 3.6% |
| Isopropyl Palmitate | 3.6% |
| Caprylic/Capric Triglyceride | 3.6% |
| Dimethicone | 1.0% |
| Phenoxyethanol Ethylhexylglycerin[1] | 0.7% |

[1] Euxyl PE 9010 (Schülke)
[2] TEGIN M (Evonik Industries AG)

Sunscreen emulsion with SPF 50

| Example 1 | 3.0% |
|---|---|
| Glyceryl Stearate | 2.0% |
| Stearyl Alcohol | 1.5% |
| Stearic acid | 2.0% |
| C12-15 Alkyl Benzoate | 5.0% |
| Phenoxyethanol Caprylate | 2.0% |
| Diethylhexyl Carbonate | 3.0% |
| Dimethicone | 1.0% |
| Butyl Methoxydibenzoylmethane | 5.0% |
| Octocrylene | 10.0% |
| Triacontanyl PVP[3] | 2.0% |
| Titanium Dioxide: Silica: Glycerin[4] | 5.5% |
| Titanium Dioxide: Silica[5] | 7.5% |
| Demineralized Water | ad 100% |
| Glycerin | 3.0% |
| EDTA | 0.1% |
| Cetearyl Glucoside[6] | 2.0% |
| Polyquaternium-37[7] | 1.0% |
| Phenoxyethanol Ethylhexylglycerin[1] | 0.7% |

[3] Ganex WP-660 (Ashland Specialty Chemicals)
[4] UV Titan M040 (Merck Performane Materials)
[5] Eusolx T-Avo (Merck Performance Materials)
[6] TEGO Care CG 90 (Evonik Industries AG)
[7] Cosmedia Ultragel 300 (BASF Personal Care and Nutrition GmbH)

Antiperspirant/Deodorant Lotion

| Example 2 | 1.0% |
|---|---|
| Steareth-2 | 3.0% |
| Steareth-20 | 2.0% |
| Diethylhexyl Carbonate | 3.0% |
| PPG-14 Butyl Ether | 3.0% |
| Polyglyceryl-3 Caprylate | 0.5% |
| Demineralized Water | ad 100% |
| Hydroxyethylcellulose[8] | 1.0% |
| Aluminum chlorohydrate (50% strength)[9] | 15.0% |
| Phenoxyethanol Ethylhexylglycerin[1] | 0.8% |

[8] Natrosol 250 HHR (Ashland Specialty Chemicals)
[9] Reach 501L (Reheis)

Lotion with Cosmetic Active Ingredients

| Example 2 | 2.0% |
|---|---|
| Polyglyceryl-6 Stearate: Polyglyceryl-6 Behenate[10] | 1.5 |
| Glyceryl Stearate | 0.5% |
| Cetearyl Alcohol | 0.5% |
| Caprylic/Capric Triglyceride | 8.5% |
| Ethylhexyl Palmitate | 8.5% |
| Demineralized Water | ad 100% |
| Polyquaternium-37[7] | 0.8% |
| Tetrapeptide-21: Glycerin: Butylene Glycol: Aqua[11] | 0.5% |
| Creatine[12] | 0.2% |
| Caffeine | 0.2% |
| Phenoxyethanol, Methylparaben, Propylparaben; Ethylhexylglycerin[13] | 1.0% |

[10] TEGO Care PBS 6 (Evonik Industries AG)
[11] TEGO Pep 4-17 (Evonik Industries AG)
[12] TEGO Cosmo C 100 (Evonik Industries AG)
[13] Phenonip XB (Clariant International Ltd.)

O/W Serum

| Example 2 | 3.0% |
|---|---|
| Cetearyl Glucoside[6] | 0.5% |
| Glyceryl Stearate | 0.75% |
| Stearyl Alcohol | 0.75% |
| Caprylic/Capric Triglyceride | 2.0% |
| Oleyl Erucate | 2.0% |
| Isoamyl Cocoate | 3.0% |
| Persea Gratissima (Avocado) Oil | 1.0% |
| Aqua; Ethylhexyl Stearate; Sodium Hyaluronate Crosspolymer; Polyglyceryl-4 Diisostearate/ Polyhydroxystearate/Sebacate: Sodium Isostearate[14] | |
| Demineralized Water | ad 100% |
| Butylene Glycol | 5.0% |
| Tetrapeptide-21: Glycerin: Butylene Glycol: Aqua[11] | 2.0% |
| Hydrolyzed Hyaluronic Acid[15] | 0.1% |
| Polyquaternium-37[7] | 0.5% |
| Phenoxyethanol Ethylhexylglycerin[1] | 0.8% |

[14] HYACARE Filler CL (Evonik Industries AG)
[15] HYACARE 50 (Evonik Industries AG)

Sprayable Lotion

| Example 2 | 4.5% |
|---|---|
| Glycerin | 4.0% |
| Demineralized Water | ad 100% |
| Diethylhexyl Carbonate | 2.5% |
| Isopropyl Palmitate | 4.25% |
| Ceteareth-25 | 1.5% |
| Stearyl Alcohol | 4.0% |

-continued

| Example 2 | 4.5% |
|---|---|
| Cetyl Dimethicone[16] | 2.5% |
| Mineral Oil | 1.0% |
| Phenoxyethanol | 0.7% |
| Ethylhexylglycerin[1] | |

[16] ABIL Wax 9801 (Evonik Industries AG)

Cationic Sunscreen

| Example 1 | 5.0% |
|---|---|
| Glyceryl Stearate | 1.0% |
| Stearyl Alcohol | 1.0% |
| Cetearyl Alcohol | 1.0% |
| C12-15 Alkyl Benzoate | 4.0% |
| Diethylhexyl Carbonate | 3.0% |
| Cetyl ricinoleate | 1.0% |
| Triisostearine | 1.0% |
| Butyl Methoxydibenzoylmethane | 2.0% |
| Ethylhexyl Salicylate | 4.0% |
| Octocrylene | 7.0% |
| Creatine[12] | 0.5% |
| Glycerin | 3.0% |
| Demineralized Water | ad 100% |
| Phenoxyethanol | 0.7% |
| Ethylhexylglycerin[1] | |

Cationic Foundation

| Example 4 | 4.8% |
|---|---|
| Glyceryl Stearate | 1.0% |
| Stearyl Alcohol | 1.0% |
| Cetearyl Alcohol | 1.0% |
| Ethylhexyl Palmitate | 4.0% |
| Diethylhexyl Carbonate | 4.0% |
| Titanium Dioxide[17] | 8.0% |
| Iron Oxide[18] | 4.0% |
| Iron Oxide[19] | 1.8% |
| Iron Oxide[20] | 0.4% |
| Glycerin | 3.0% |
| Demineralized Water | ad 100% |
| Phenoxyethanol | 0.7% |
| Ethylhexylglycerin[1] | |

[17] Hombitan AC 360 (Sachtleben)
[18] Unipure Yellow LC 182 (Sensient Technologies)
[19] Unipure Red LC 381 (Sensient Technologies)
[20] Unipure Black LC 989 (Sensient Technologies)

O/W Soft Cream

| Example 3 | 2.0% |
|---|---|
| Bis-PEG/PPG-16/16 PEG/PPG-16/16 Dimethicone: Caprylic/Capric Triglyceride[21] | 1.0% |
| Glyceryl Stearate | 2.5% |
| Cetearyl Alcohol | 1.5% |
| Cetearyl Ethylhexanoate | 9.0% |
| Caprylic/Capric Triglyceride | 9.0% |
| Glycerin | 8.0% |
| Demineralized Water | ad 100% |
| Phenoxyethanol, Methylparaben, Propylparaben; Ethylhexylglycerin[13] | 0.7% |

[21] ABIL Care 85 (Evonik Industries AG)

O/W Blemish Balm Lotion

| Example 1 | 2.0% |
|---|---|
| Polyglyceryl-6 Stearate: Polyglyceryl-6 Behenate[10] | 2.0% |
| Glyceryl Stearate | 0.75% |
| Stearyl Alcohol | 0.75% |
| Diethylhexyl Carbonate | 7.40% |
| Ethylhexyl Methoxycinnamate | 5.00% |
| Diethylamino Hydroxybenzoyl Hexyl Benzoate[22] | 3.00% |
| Phytosphingosine | 0.10% |
| Hydrolyzed Hyaluronic Acid[15] | 0.10% |
| Tetrapeptide-21: Glycerin: Butylene Glycol: Aqua[11] | 2.00% |
| Demineralized Water | ad 100% |
| Titanium Dioxide[17] | 3.00% |
| Talc | 2.00% |
| Iron Oxide[18] | 0.36% |
| Iron Oxide[19] | 0.12% |
| Iron Oxide[20] | 0.08% |
| Isoamyl Cocoate | 4.44% |
| Phenoxyethyl Caprylate | 4.00% |
| Nylon-10/10[23] | 3.00% |
| Glycerin | 3.00% |
| Polyquaternium-37[7] | 0.50% |
| Ethanol | 3.00% |
| Methylisothiazolinone, Methylparaben, Ethylparaben; Dipropylene, Glycol[24] | 0.80% |

[22] Uvinul A Plus (BASF SE)
[23] TEGOLON ECO 10-10 (Evonik Industries AG)
[24] Microcare MEM (Thor Personal Care)

Preservative-Free Lotions

| Example 2 | 3.0% | 3.0% |
|---|---|---|
| Glyceryl Stearate | 0.5% | 0.5% |
| Stearyl Alcohol | 0.5% | 0.5% |
| Prunus Amygdalus Dulcis (Sweet Almond) Oil | 10.0% | 10.0% |
| Isoamyl Cocoate | 6.0% | 6.0% |
| Glycerin | 4.0% | 4.0% |
| Demineralized Water | ad 100.0% | ad 100.0% |
| Caprylyl Glycol. Glycerin. Glyceryl Caprylate. Phenylpropanol[25] | 1.0% | |
| Methylpropanediol. Caprylyl Glycol. Phenylpropanol[26] | | 4.0% |
| Polyquaternium-37[7] | 0.5% | 0.5% |

[25] Dermosoft LP (Dr. Straetmans Chemische Produkte GmbH)
[26] Dermosoft OMP (Dr. Straetmans Chemische Produkte GmbH)

O/W Soft Cream

| Example 2 | 2.0% |
|---|---|
| Bis-PEG/PPG-16/16 PEG/PPG-16/16 Dimethicone: Caprylic/Capric Triglyceride[21] | 1.0% |
| Glyceryl Stearate | 2.5% |
| Cetearyl Alcohol | 1.5% |
| Diethylhexyl Carbonate | 5.0% |
| Dimethicone | 5.0% |
| Dimethicone/Vinyl Dimethicone Crosspolymer[27] | 0.5% |
| Cyclopentasiloxane: Dimethicone Crosspolymer[28] | 5.0% |
| Glycerin | 3.0% |
| Demineralized Water | ad 100% |
| Methylisothiazolinone, Methylparaben, Ethylparaben; Dipropylene, Glycol[24] | 0.8% |

[27] KSG-15 (Shin Etsu)
[28] DC 9045 Elastomer Blend (Dow Corning)

European patent application EP 15174954.6 filed Jul. 2, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. An emulsion, comprising:
   A) from 0.5% by weight to 10% by weight of an alkyl ester quat of formula I

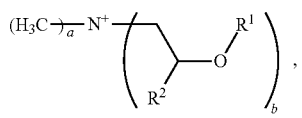

wherein $R^1$ is an acyl radical from a saturated, linear fatty acid with a chain length of from 16 to 18 carbon atoms, $R^2$ is methyl, and
   a=1.8-2.2 and b=1.8-2.2, with the proviso that a+b=4;
   B) from 2% by weight to 10% by weight of at least one consistency regulator selected from the group consisting of fatty alcohols having 12 to 24 carbon atoms, glycerol esters, polyglyceryl esters, fatty acids having 12 to 24 carbon atoms, polymer-based thickeners and mixtures thereof; and
   C) from 6% by weight to 30% by weight of at least one cosmetic oil selected from the group consisting of silicone oils, functionalized silicones, mineral oils, fatty acid esters, fatty alcohol ethers, natural oils, animal oils and mixtures thereof,
   wherein the percent by weight of the amounts of components A), B), and C) are based on a weight of the total emulsion.

2. The emulsion according to claim 1, wherein a mass fraction of $R^1$ from a saturated, linear fatty acid with a chain length of 18 carbon atoms is more than 60% by weight, based on all acyl radicals $R^1$.

3. The emulsion according to claim 1, wherein the component A) is free of solvent.

4. The emulsion according to claim 1, wherein the component A) is free of isopropyl alcohol.

5. A cosmetic care and/or cleaning formulation, comprising:
   the emulsion according to claim 1.

6. The emulsion according to claim 1, wherein
   the component A) comprises methyldiisopropanolamine (MDIPA) dialkyl quat with stearic acid,
   the component B) is at least one selected from the group consisting of glyceryl stearate and cetearyl alcohol, and
   the component C) is at least one selected from the group consisting of mineral oil, isopropyl palmitate, caprylic/capric triglyceride, and dimethicone.

7. The emulsion according to claim 1, comprising:
   from 1% by weight to 6% by weight of the component A), and
   from 3% by weight to 6% by weight of the component B),
   wherein the percent by weight of the amounts of components A) and B) are based on a weight of the total emulsion.

8. The emulsion according to claim 1, wherein the emulsion does not exhibit water separation when stored for three months at 45° C.

9. The emulsion according to claim 8, wherein the emulsion does not exhibit water separation after a triple freeze-thaw cycle between room temperature and −15° C.

* * * * *